United States Patent [19]
Dixit

[11] Patent Number: 5,688,656
[45] Date of Patent: Nov. 18, 1997

[54] CYTOKINE-INDUCED MARKER FOR INFLAMMATORY RESPONSE

[75] Inventor: Vishva M. Dixit, Ann Arbor, Mich.

[73] Assignee: The Regents of the University of Michigan, Ann Arbor, Mich.

[21] Appl. No.: 441,216

[22] Filed: May 15, 1995

Related U.S. Application Data

[62] Division of Ser. No. 321,162, Oct. 11, 1994, Pat. No. 5,599,669, which is a continuation of Ser. No. 164,611, Dec. 8, 1993, abandoned, which is a continuation of Ser. No. 607,741, Oct. 16, 1990, abandoned.

[51] Int. Cl.$^6$ .......................... C07K 14/47; C07K 16/18; G01N 33/536; G01N 33/543
[52] U.S. Cl. .......................... 435/7.21; 435/69.1; 436/518; 436/536; 530/388.23; 530/389.2; 530/395
[58] Field of Search .................................. 435/7.1, 7.21; 436/518, 536, 69.1; 530/388.23, 389.2, 395

[56] References Cited

FOREIGN PATENT DOCUMENTS 0597503  5/1994  European Pat. Off. .

OTHER PUBLICATIONS

Yoshimura, T. et al., "Purification and amino acid analysis of two human glioma–derived monocyte chemoattractants", *J. Exp. Med.* 169:1449–1459 (1989).

Ausubel, F. M. et al., Current Protocols in Molecular Biology, Greene Publishing Associates (1993).

Boguski, M. S. et al., "On computer–assisted analysis of biological sequences: proline punctuation, consensus sequences, and apolipoprotein repeats", *J. Lipid. Res.* 27:1011–1034 (1986).

Caput, D. B. et al., "Identification of a common nucleotide sequence in the 3'–untranslated region of mRNA molecules specifying inflammatory mediators", *PNAS (USA)* 83:1670–1674 (1986).

Dieckmann, C. L. et al., "Assembly of the mitochondiral membrane system. CBP6, a yeast nuclear gene necessary for synthesis of cytochrome b", *J. Biol. Chem.* 266:1513–1520 (1985).

Dixit, V. M. et al., "The antimitogenic action of tumor necrosis factor is asscoiated with increased AP–1/c–jun proto–oncogene transcription", *J. Biol. Chem.* 264:16905–16909 (1989).

Feinberg, A. P. et al., "A technique for radiolabelling DNA restriction endonuclease fragments to high specific activity", *Anal. Biochem.* 132:6–13 (1983).

Fraker, P. J. et al., "Protein and cell membrane iodinations with a sparingly soluble chloroamide, 1,3,4, 6–tetrachloro–3a,6a–diphenylglycoluril", *Biochem. Biophys. Res. Commun.* 80:849–857 (1978).

Harlow, E. et al., *Antibodies: A Laboratory Manual*, Cold Spring Harbor Laboratory, Cold Spring Harbor, N.Y. :471–510 (1988).

Jansen, R. et al., "Cloning of a full length methylmalonyl–CoA mutase from a cDNA library using the polymerase chain reaction", *Genomics* 4:198–205 (1989).

Kozak, M., "The scanning model for translation : An update", *J. Cell. Biol.* 108:229–241 (1989).

Kyte, J. et al., "A simple method for displaying the hydropathic character of a protein", *J. Mol. Biol.* 157:105–132 (1982).

Maizel, J. V. et al., "Enhanced graphic matrix analysis of nucleic acid and protein sequences", *PNAS (USA)* 78:7665–7669 (1981).

Pearson, W. R. et al., "Improved tools for biological sequence comparison", *PNAS (USA)* 85:2444–2448 (1988).

Prochownik, E. V. et al., "Expression and analysis of COOH–terminal deletions of the human thromospondin molecule", *J. Cell. Biol.* 109:843–852 (1989).

Sambrook, J. et al., *Molecular Cloning: A Laboratory Manual*, Second ed. Cold Spring Harbor Laboratory, Cold Spring Harbor, N.Y. (1989) pp. 15.81–15.84 and 7.53–7.57.

Spindler, K. R. et al., "Analysis of adenovirus transforming proteins from early regions 1A and 1B with antisera to inducible fusion antigens produced in *Escherichia coli*", *J. Virol.* 49:132–141 (1984).

Bevilacqua, M. P. et al., "Endothelial Leukocyte Adhesion Molecule 1: An inducible receptor for neutrophils related to complement regulatory proteins and lectins", *Science* 243:1160–1165 (1989).

Bevilacqua, M. P. et al., "Interleukin 1(IL–1) induces biosynthesis and cell surface expression of procoagulant activity in human vascular endothelial cells", *J. Exp. Med.* 160:618–623 (1984).

Bevilacqua, M. P. et al., "Interleukin 1 acts on cultured human vascular endothelium to increase the adhesion of polymorphonuclear . . . lines", *J. Clin. Invest.* 76:2003–2011 (1985).

Bevilacqua, M. P. et al., "Recombinant tumor necrosis factor induces procoagulant activity in cultured vascular endothelium: characterization and comparison with the actions of interleukin 1" *PNAS (USA)* 83:4533–4537 (1986).

Broudy, V. C. et al., "Interleukin 1 stimulates human endothelial cells to produce granulocyte–macrophage colony–stimulating factor and granulocyte colony–stimulating factor", *J. Immunol.* 139:464–468 (1987).

Brown, K. D. et al., "A family of small inducible proteins secreted by leukocytes are members of a new superfamily that includes leukocyte and fibroblast–derived inflammatory agents, growth factors, and indicators of various activation processes", *J. Immunol.* 142:679–687 (1989).

(List continued on next page.)

*Primary Examiner*—David Saunders
*Attorney, Agent, or Firm*—Morrison & Foerster LLP

[57] ABSTRACT

A gene and its gene product which is a marker for inflammatory response have been identified, cloned and sequenced. With the identification of the B61 gene and its product, protein assays of biological fluids as well as nucleic acid probes and antibodies raised to the gene product can be used in a variety of hybridization and immunological assays to detect an impending inflammatory response. Such detection will enable earlier administration of appropriate therapy in immune response diseases.

14 Claims, 8 Drawing Sheets

OTHER PUBLICATIONS

Dustin, M. L. et al., "Lymphocyte function–associated antigen–1 (LFA–1) interaction with intercellular adhesion molecule–1(ICAM–1) is one of at least three mechanisms for lymphocyte adhesion to cultured endothelial cells", *J. Cell Biol.* 107:321–331 (1988).

Leonard, E. J. et al., "Human monocyte chemoattractant protein–1 (MCP–1)" *Immunol. Today* 11:97–101 (1990).

Libby, P. et al., "Interleukin 1: a mitogen for human vascular smooth muscle cells that induces the release of growth–inhibitory prostanoids", *J. Clin. Invest.* 81:487–498 (1988).

Locksley, R. M. et al., "Tumor necrosis factors alpha and beta differ in their capacities to generate interleukin 1 release from human endothelial cells", *J. Immunol.* 139:1891–1895 (1987).

Mantovani, A. et al., "Cytokines as communication signals between leukocytes and endothelial cells", *Immunol. Today* 10:370–375 (1989).

Nawroth, P. P. et al., "Modulation of endothelial cell hemostatic properties by tumor necrosis factor", *J. Exp. Med.* 163:740–745 (1986).

Robinson, E. A. et al., "Complete amino acid sequence of human monocyte chemoattractant, a putative mediator of cellular immune reactions", *PNAS (USA)* 86:1850–1854 (1989).

Sayers, T. J. et al., "Effect of cytokines on polymorphonuclear neutrophil infiltration in the mouse. Prostaglandin–and leukotriene–independent induction of infiltration by IL–1 and tumor necrosis factor", *J. Immunol.* 141:1670–1677 (1988).

Ferguson, N. A. et al., "Cell–surface enchoring of proteins via glycosylphosphatidylinositol structures", *Ann. Rev. Biochem.* 57:285–320 (1988).

von Heijne, G., "Signal sequences: the limits of variation", *J. Mol. Biol.* 184:99–105 (1985).

Von Heijne, G., "A new method for predicting signal sequence cleavage sites", *Nucl. Acids Res.* 14:4683–4690 (1986).

Furley, A. J. et al., "The axonal glycoprotein TAG–1 is an immunoglobulin superfamily member with neurite outgrowth–promoting activity", *Cell* 61:157–170 (1990).

Gower, H. J. et al., "Alternate splicing generates a secreted form of NCAM in muscle and brain", *Cell* 55:955–964 (1988).

Dixit, V. M. et al., "Tumor necrosis factor–alpha Induction of novel gene products in human endothelial cells including macrophage–specific chemotaxin", *J. Biol. Chem.* 265:2973–2978 (1990).

Cochran, B. H. et al., "Molecular cloning of gene sequences regulated by platelet–derived growth factor", *Cell* 33:939–947 (1983).

Cochran, B. H. et al., "Expression of the c–fos gene and of an fos related gene is stimulated by platelet–derived growth factor", *Science J.* 226:1080–1082 (1984).

Kelly, K. et al., "Cell–specific regulation of the c–myc gene by lymphocyte mitogens and platelet–derived growth factor", *Cell* 35:603–610 (1983).

Schleef, R. R. et al., "Cytokine activation of vascular endothelium. Effects on tissue–type plasminogen activator and type 1 plasminogen activator inhibitor", *J. Biol. Chem.* 263:5797–5803 (1988).

Seelentag, W. K. et al., "Additive effects of interleukin 1 and tumor necrosis factor–alpha on the accumulation of the three granulocyte and macrophage colony–stimulating factor mRNAs in human endothelial cells", *EMBO J.* 6:2261–2265 (1987).

Sieff, C. A. et al., "Interleukin–1, tumor necrosis factor, and the production of colony–stimulating factors by cultured mesenchymal cells", *Blood* 72: 1316–1323 (1988).

Sironi, M. et al., "IL–1 stimulates IL–6 production in endothelial cells", *J. Immunol.* 142:549–553 (1989).

Strieter, R. M. et al., "Endothelial cell gene expression of a neutrophil chemotactic factor by TNF–alpha, LPS, and IL–1 beta", *Science* 243:1467–1469 (1989).

Yoshimura, T. et al., "Human monocyte chemoattractant protein–1 (MCP–1). Full length cDNA cloning, expression in m togen–stimulated blood mononuclear leukocytes, and sequence similarity to mouse competence gene JE" *FEBS Lett.* 244:487–493 (1989).

Toneguzzo, F. et al., "Use of a chemically modified 17 polymerase for manual and automated sequencing of super-coiled DNA", *Biotechniques* 6:460–468 (1988).

Wilbur, W. J. et al., "Rapid similarity searches of nucleic acid and protein data banks", *PNAS (USA)* 80:726–730 (1983).

"Biochemicals for Molecular Biology", Boehringer Mannheim Chemicals,p. 144.

Corbi et al., "cDNA cloning and complete primary structure of the a subunit of a leukocyte adhesion glycoprotein", p150.95 *EMBO J.* (1987) 6:4023–4028.

Beckman et al., "The structure and evolution of a 461 amino acid human protein C precursor and its messenger RNA, based upon the DNA sequence of cloned human liver cDNAs" *Nucleic Acids Research* (1985) 13:5233–5247.

Crompton et al., "Identification of a novel vertebrate homeobox gene expressed in haematopoietic cells" *Nucleic Acids Research* (1992) 20:5661–5667.

FIG. 3A

```
  -74  GCGGAGAAAGCCAGTGGGAACCAGACCCATAGGAGAACCCGCTCCCGCTCCCGCTCGGCTGCCAGGCCCCGCTATGGAGTTCCTCTGGGCCCCTCTTG
                                                                              M  E  F  L  W  A  P  L  L       9
   27  GGTCTGTGCTGCAGTCTGGCCGCTGCTGATCGCCACACCGTCTTCTGAAGATCACTCTGTCCGCACTATGAAGATGAGGACTACACCATACATGTGCAGC
         G  L  C  C  S  L  A  A  A  D  R  H  T  V  F  W  N  S  S  N  P  K  F  R  N  E  D  Y  T  I  H  V  Q  L     43
  127  TGAATGACTACGTGGACATCATCTGTCCGCACTATGAAGATCACTCTGTGGCAGATGCCGCCATGGAGCAGTACATACTGTACTGTGGAGAAGTTCCAG
         N  D  Y  V  D  I  I  C  P  H  Y  E  D  H  S  V  A  D  A  A  M  E  Q  Y  I  L  Y  L  V  E  H  E  E      76
  227  GTACCAGCTGTGCCAGCCCCAGTCCAAGGACCAAGTCCGCTGGCAGTGCAACCGGCCCAGTGCCAAGCATGGCCCGGAGAAGCTGTCTGAGAAGTTCCAG
         Y  Q  L  C  Q  P  Q  S  K  D  Q  V  R  W  Q  C  N  R  P  S  A  K  H  G  P  E  K  L  S  E  K  F  Q     109
  327  CGCTTCACACCTTTCACCCTGGGCAAGGAGTTCAAAGAAGGAGACACAGCTACTACATCCAAACCATCCACAGAGAAGACTACTTGCAGCAGCCTGAGGT
         R  F  T  P  F  T  L  G  K  E  F  K  E  G  H  S  Y  Y  Y  I  S  K  P  I  H  Q  H  E  D  R  C  L  R  L  143
  427  TGAAGGTGACTGTCAGTGGCAAAATCACTCACAGTCCTCAGGCCCATTGCCTGGACTGTGCTCCTTCCACTTCTGCTGTGCTGCAAACCCGTGAAGGTGTATG
         K  V  T  V  S  G  K  I  T  H  S  P  Q  A  H  V  N  P  Q  E  K  R  L  A  A  D  D  P  E  V  R  V  L     176
  527  ACATAGCATCGGTCACAGTGGCCTTAAAGAGGACAGCTGAAGAGCTGAAGAGAGGACAGGGACACTCCAAACCTGTCTTCAGAGCCCCACTTTCAGAGCCCCTGGGAACCACTCC
         H  S  I  G  H  S  A  A  P  R  L  F  P  L  A  W  T  V  L  L  L  P  L  L  L  Q  T  P  *                205
  627  CCACACCTGGCCTTAAAGAGGACAGCTGAAGAGCTGAAGAGAGGACAGGGACACTCCAAACCTGTCTTCAGAGCCCCACTTTCAGAGCCCCTGGGAACCACTCC
  727  CACCACAGGCATAAGCTATCACCTAGCAGCCTCAAAACGGGTCAGTATTAAGGTTTCAACCGGAAGGAGGCCAACCAGCCCGACAGTGCCATCCCACC
  827  TTCACCTCGGAGGGACGGAGAAGAAGTGGAGACAGTCCTTTCCGCCATTCCTGCCTTTAAGCCAAAGAAACAAGCTGTGCAGGCATGGTCCTTAAGG
  927  CACAGTGGGAGCTGAGCTGGAAGGGCCACGTGGCCCATGTGCCCATGTCCCAGGAGATGCCCAGAGAGCAGGATGCCCAGATGCCCAGAAGATGAACTGACTGA
 1027  AGGAAAAGCAAGAAACAGTTCTTGCTTGGAGCCCAGGTACAGGAGAGGCAGCAGTGCTTGGGCTGACCAGCATCTCCCAGCAAGACCTCATCTGTGGAG
 1127  CTGCCACAGAGAAGTTTGTAGCCAGGTACTGCATTCTCTCCCATCCTGGGCAGCACTCCCCAGAGCTGTGCCAGGGGGCTGTGCCAACCTGTTCT
 1227  TAGAGTGTAGCTGTAAGGGCAGTGCCCATGTGCCTAAAGGGCAGGGCCCACGTGTAGTGTAGCCTAAAGGGCAGGGCCCACGTGTAGTATCTGTATATAAGTTGCTG
 1327  TGTGTCTGTCCTGATTTCTACAACTGGAGTTTTTTATACAATGTTCTTGTCTCAAATAAAGCAATGTGTTTTTTCGGAAAAAAAAAAAAAAAAAAAA
```

CYTOKINE-INDUCED MARKER FOR INFLAMMATORY RESPONSE

This application is a divisional application of U.S. Ser. No.: 08/321,162, filed Oct. 11, 1994, now U.S. Pat. No. 5,599,669, issued Feb. 4, 1997, which is a continuation of U.S. Ser. No. 08/164,611, filed Dec. 8, 1993, now abandoned, which in turn is a continuation of application U.S. Ser. No. 07/607,741, filed Oct. 16, 1990, now abandoned.

This invention was made in part with governmental support under National Institutes of Health Grant HL39415. The government has certain rights to this invention.

FIELD OF THE INVENTION

The present invention relates generally to a gene involved in the inflammatory response and, more particularly, to the identification, isolation and cloning of a nucleic acid sequence corresponding to the gene. The present invention also relates to methods of using the gene product as a marker for inflammation.

BACKGROUND OF THE INVENTION

Inflammation is a complex response to injury in which the immune system is activated and responds by attempting to nullify the noxious stimulus. In certain situations, however, an inappropriate immune response, often directed against host antigens, results in autoimmune diseases, such as rheumatoid arthritis, temporal arthritis, gout, systemic lupus erythematosis and possibly multiple sclerosis. These chronic degenerative disease states are usually treated aggressively with anti-inflammatory drugs and steroids. However, such therapy is often instituted after the inflammatory process is already well progressed. Cellular markers whose expression antedates a histologically obvious inflammatory response would thus clearly be useful in predicting relapses in autoimmune diseases and would allow the earlier initiation of anti-inflammatory therapy and attenuation of the disease process.

The search for such cellular markers began with the recognition that the vascular endothelium plays an active central role in the process of acute inflammation. Under the influence of proinflammatory cytokines such as tumor necrosis factor-$\alpha$, (TNF-$\alpha$) and interleukin-1$\beta$ (IL-1$\beta$), endothelial cells convert from an anticoagulant to a procoagulant phenotype, induce leukocyte adhesion and chemotaxis and secrete cytokines important for hematopoiesis, leukocyte activation, and smooth muscle cell proliferation. While TNF and IL-1 are not directly chemotactic, they induce endothelial cells to secrete chemotactic factors such as interleukin-8 (monocyte-derived neutrophil chemotactic factor) and monocyte chemoattractant protein 1. Adhesion of leukocytes to stimulated endothelium is facilitated by the cytokine mediated increased plasma membrane expression of intercellular adhesion molecule 1 and endothelial leukocyte adhesion molecule 1. The activated endothelium further contributes to establishing the inflammatory response by secreting additional IL-1 as well as interleukin-6 (IL-6), and several colony stimulating factors, which induce leukocyte activation and participate in the differentiation and proliferation T and B cells.

Recently a group of eight TNF-$\alpha$, induced immediate-early response genes derived from cultured human umbilical vein endothelial (HUVE) cells was cloned using differential hybridization. See Dixit, V. M. et al., *J. Biol. Chem.* 265:2973-2978 (1990). Of the eight gene products, two were chemotactic cytokines, interleukin-8 (IL-8) and monocyte chemoattractant protein 1, and two were adhesion molecules, endothelial leukocyte adhesion molecule 1 and intercellular adhesion molecule 1. The gene products of the remaining four primary response genes, including the product of the gene of the present invention, had not been previously described.

SUMMARY OF THE INVENTION

A gene involved in early inflammatory response, hereinafter "B61 gene" or "gene for B61", and its transcript of approximately 25 kDa have been isolated, cDNA cloned and sequenced in accordance with the present invention. The cDNA sequence of the invention is set forth in FIG. 3A and SEQ ID NO:1. The gene product, hereinafter "B61", is a relatively small molecule with a predicted mature protein length of 187 amino acids as shown in FIG. 3A and SEQ ID NO:2. It will be appreciated that the nucleotide and amino acid sequences of the present invention can include some variation from FIG. 3A and SEQ ID NOS:1 and 2, but must be "substantially similar" to those set forth therein. By "substantially similar" is meant that any variation therein does not impair the functionality of the sequence to any significant degree.

B61 is primarily a hydrophilic molecule but contains both a hydrophobic N-terminal and a hydrophobic C-terminal region. B61 is secreted by endothelial cells, fibroblasts and keratinocytes in response to lipopolysaccharide and the proinflammatory cytokines IL-1 and TNF. The B61 gene product is not, however, induced in response to other agents such as growth factors and interferon. The induction of B61 is thus highly specific, occurring only in response to proinflammatory stimuli.

In accordance with the principles of the present invention, B61 serves as a marker for impending inflammatory responses. The presence of B61 transcript can be detected directly by in situ hybridization using probes of encoding cDNA. Alternatively, the B61 protein can be measured in biological fluids such as plasma, cerebrospinal fluid or urine using an antibody-based assay. These assay procedures of the present invention make it possible to predict a worsening in the disease process and allow quantitative assessment of the magnitude of the inflammatory response. This information will enable earlier administration of appropriate therapy, thereby shortening the disease process itself and limiting the patient's exposure to anti-inflammatory/immunosuppressive therapy.

Other features and advantages of the present invention will be become apparent from the following description and appended claims, taken in conjunction with the accompanying drawings.

BRIEF DESCRIPTION OF THE DRAWINGS

FIG. 3A depicts the B61 nucleotide and predicted amino acid sequences also set forth in SEQ ID NOS:1 and 2.

DETAILED DESCRIPTION OF THE PREFERRED EMBODIMENTS

Figure 1:
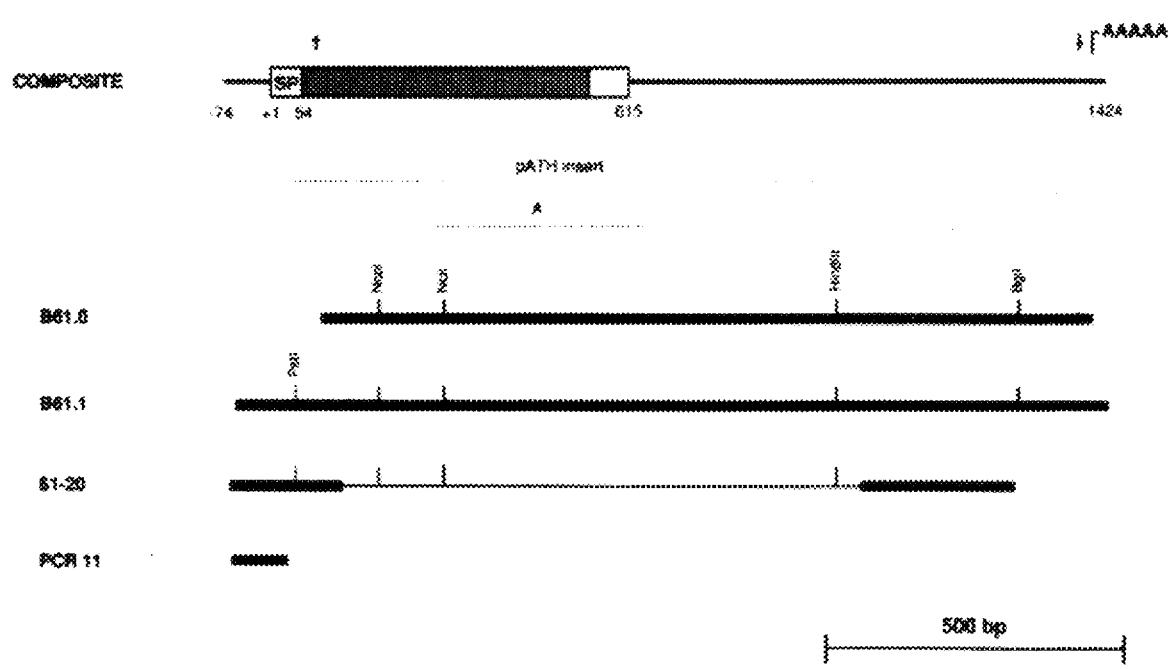
FIG. 1 is a schematic representation of B61 mRNA and cloning strategy.

B61 is a novel secreted protein whose expression is rapidly induced (about 30 minutes) in endothelial cells following stimulation with the proinflammatory cytokines tumor necrosis factor-α (TNF-α) and interleukin-1β (IL-1β). Comparison of the sequence of the cDNA clones encoding B61 to sequence library data demonstrates that this protein has no significant homology to previously identified proteins. The B61 protein has several important structural features. Amino acid sequence analysis reveals that the mature form is a relatively small protein of 187 amino acid residues, with a predicted molecular weight of 22 kDa. On reducing SDS-PAGE, B61 migrates as a 25 kDa protein. This difference could be due to glycosylation or other post-translational modifications. Indeed, a single site for N-linked glycosylation exists at the N-terminus of the predicted mature form of the protein.

Members of the small inducible and secreted protein (SIS) superfamily such as human monocyte chemoattractant protein 1 (hMCP-1, the human homolog of mouse JE), human platelet factor 4, and human interleukin-8, are all expressed in human umbilical vein epithelium (HUVE) in response to activation stimuli, and can act as proinflammatory cytokines. See Leonard, E. J. et al., *Immunol. Today* 11:97–101 (1990). Like the members of this superfamily, B61 is also a small, secreted, cytokine inducible gene product. However, despite the presence of four cysteine residues in the mature form of B61, this protein does not appear to be a member of the SIS family; the spacing of cysteines in B61 is not similar to the spacing found in SIS proteins which with minor exception is invariably conserved. See Brown, K. D. et al., *J. Immunol.* 142:679–687 (1989).

Analysis of hydrophobicity shows that B61 is primarily hydrophilic, but possesses both an N-terminal and C-terminal hydrophobic domain. The N-terminal domain has a well-defined signal peptide structure as described by von Heijne, G., *J. Mol. Biol.* 184:99–105 (1985), which is consistent with the secreted nature of B61. With respect to the C-terminal hydrophobic domain, while this segment spans 23 amino acid residues, it appears unlikely that it represents a transmembrane segment since it is interrupted by polar residues. Moreover, no basic amino acid residues typical of a membrane retention signal are found on the C-terminal side of this region. Although no clear consensus sequence exists for glycosyl-phosphatidylinositol-linked membrane anchored proteins, the B61 C-terminus bears striking structural similarity to the hydrophobic C-terminus of many of these proteins. In GPI-linked proteins, the hydrophobic C-terminus is thought to function as a signal for BPI attachment and is cleaved during post-translational linkage steps as discussed in Ferguson, M. A. et al., *Ann. Rev. Biochem.* 57:285–320 (1988). Despite the similarity, B61 has not been associated with the plasma membrane of TNF-stimulated HUVE in culture has not been detected. Since GPI-linked proteins such as neural cell adhesion molecule and TAG-1 are found in both a membrane associated form and released form (see Furley, A. J. et al., *Cell* 61:157–170 (1990) and Gower, H. J. et al., *Cell* 55:955–964 (1988)), it remains possible that B61 also exists in both a-plasma membrane bound and a secreted form under conditions other than those tested. Further, since B61 expression is not endothelial cell specific, a membrane associated form may be expressed in cells other than HUVE.

TNF dramatically affects endothelial cell function by promoting a pleiotropic response which includes a proinflammatory phenotype. The changes induced by TNF were investigated, with the analysis focusing on the cloning of cellular immediate-early genes. Such genes undergo rapid and profound induction independent of intermediary protein synthesis. Based on the results of earlier work, in which E and KC (see Cochran, B. H. et al., *Cell* 33:939–947 (1983)), as well as c-myc and c-fos (see Cochran, B. H. et al., *Science* 226:1080–1082 (1984); Kelly, K. et al., *Cell* 35:603–610 (1983)) were found to be immediate-early response genes, it was postulated that other gene products would be identified which were either paracrine factors essential for mediating the interactions of the activated endothelial cell with its environment, or nuclear regulatory proteins capable of initiating programs with the cell. This hypothesis was borne out by the cloning of the paracrine factors, monocyte chemoattractant protein 1 and interleukin-8, as well as two adhesion molecules, ELAM 1 and ICAM 1 described by Dixit, V. M. et al., *J. Biol. Chem.* 265:2973–2978 (1990). All are essential for leukocyte recruitment and activation in acute inflammation. The newly identified secreted protein of the invention, B61, may have an equally important role in the complex proinflammatory environment.

B61 has several important features which make it useful as a marker for inflammation. Its induction is rapid and profound and thus it is easily detectable. Moreover, since it is secreted, B61 is measurable in assays, such as e.g. radio-immunoassays of bodily fluids including plasma, cerebrospinal fluid and urine. These features make it possible to monitor an inflammatory event by measuring the amount of B61 in plasma released by the inflammatory cells. In addition the B61 response is highly specific to proinflammatory stimuli, being only made by cells exposed to lipopolysaccharides or cytokines such as IL-1 and TNF and not growth factors or interferon. B61 thus fulfills the criteria for a gene product whose presence serves as an early reporter of impending inflammation.

SPECIFIC EXAMPLES

MATERIALS AND METHODS
Reagents

Recombinant human TNF-α purified from *E. coli* was a gift of Genentech (S. San Francisco, Calif.). Synthetic oligonucleotides were produced on a DNA-101 oligonucleotide synthesizer (Biotix, Danbury, Conn.) or Applied Biosystems 380A oligonucleotide synthesizer (Foster City, Calif.).

Endothelial Cells Human umbilical vein endothelial cells (HUVE) were used for all studies: They were isolated from human umbilical cords according to the method of Jaffe, E. A. Biology in Endothelial Cells. In E. A. Jaffe, (ed.) Martinus-Nijhoff, The Hague (1984) and cultured as described in Dixit, V. M. et al., *J. Biol. Chem.* 264:16905–16909 (1989). Cells were identified as endothelial on the basis of their morphology at confluence, positive immunofluorescence with antibody to human von Willebrand factor (Calbiochem) and positive staining with fluorescinated Ulex europaeus 1 lectin (Vector Laboratories, Inc., Burlingame, Calif.).

Endothelial cells for RNA extraction and metabolic radio-labelling were grown to confluence in either 150 cm² flasks (Corning, N.Y.) or 75 cm² dishes (Flacon, Cockeysville, Md.). Cells were used between the second and fourth passage. The night before extraction or labelling, culture media was removed, cells washed twice with Hank's buffered salt solution containing calcium and magnesium (Gibco), and replaced with culture media lacking endothelial cell growth factor and heparin. TNF (20 ng/ml) was added as described in individual experiments and incubated for the indicated periods. Cycloheximide (CHX), when used was added at 10 µg/ml, 30 min prior to addition of TNF. See Dixit, V. M. et al., *J. Biol. Chem.* 264:16905–16909 (1989).

cDNA Library Screening

Poly (A)$^+$ mRNA isolated from HUVE treated for 4 h with TNF and CHX was used to construct a λgt11 cDNA library, as described by Dixit, V. M. et al., *J. Biol. Chem.* 265:2973–2978 (1990). cDNA fragments derived from the 5' end of B61.0 cDNA were radiolabelled by a random hexanucleotide primer method as described by Feinberg, A. P. et al., *Anal Biochem.* 132:6–13 (1983) and used to rescreen this library. Dixit, V. M. et al., *J. Biol. Chem.* 265:2973–2978 (1990). Hybridization was performed in 50% formamide, 5× SSC (1× SSC is 0.15M sodium chloride, 0.01 5M sodium citrate), 3× Denhardt's, described by Sambrook, J. et al., Molecular Cloning: A laboratory manual. Second Edition. Cold Spring Harbor Laboaratory, Cold Spring Harbor, N.Y. (1989), 0.25% SDS, 1 µg/ml polyadenylic acid, 200 µg/ml salmon sperm DNA, and 2×10$^6$ cpm/ml $^{32}$P-labelled cDNA at 42° C. for 16 h. Filters were washed once at room temperature, followed by two 30 min washes at 65° C. in 2× SSC, 0.2% SDS. Hybridizing cDNA inserts were isolated and subcloned into pGEM 7zf(+) (Promega Corp., Madison, Wis.) for sequencing.

The polymerase chain reaction was used as described by Jansen, R. F. et al. *Genomics* 4:198–205 (1988) as an alternate approach to cloning the 5' end of the cDNA. Synthetic oligonucleotides corresponding to the region flanking the cloning site in the λgt11 phage and a region corresponding to the 5' end of partial B61 cDNA were used as primers (0.2 pM each) to amplify directly from the λgt11 cDNA library using a Cetus Gene Amp Kit. A Perkin Elmer Thermal Cycler was cycled for 1 min 15 s at 94° C., 1 min at 55° C., and 4 min at 74° C. for 35 cycles and followed by a 10 min final extension at 72° C. The amplified material was ligated to PGEM7zf(+) for sequencing.

Primer Extension

HPLC purified oligonucleotide primers were 5'-end labelled (specific activity=5×10$^6$ cpm/pmol) with γ-[$^{32}$P] ATP and T4 polynucleotide kinase (Boehringer Mannheim) and the labelled product purified on Nensorb (Dupont) columns. Thirty µg of total RNA derived from TNF and CHX treated HUVE was annealed to 1 pmole of labelled primer in a 5 mM phosphate buffer (pH 6.75) containing 5 mM EDTA. The mixture was heated to 90° C., NaCl added to final concentration for 10 mM and cooled slowly to 30° C. Extension with AMV reverse transcriptase (Seikagaku, Rockville, Md.) was carried out at 43° C. for 75 min in the presence of 10 mM DTT, 60 units RNasin, 50 mM Tris-Hcl (pH 8.3), 5.5 mM MgCl$_2$, 10 mM NaCl, and 1 mM deoxynucleotide triphosphates. Labelled products were pheno:chloroform extracted, separated on a denaturing 6% acrylamide sequencing gel, and visualized by autoradiography.

DNA Sequencing and Analysis

Plasmid DNA prepared by PEG precipitation as discussed by Ausebil, F. M. R. et al. Current Protocols in *Molecular Biology.* Greene Publishing Associated and Wiley-Interscience, N.Y.: p. 1.7.7–1.7.8 (1989) was sequenced by the dideoxy chain termination method as described by Toneguzzo, F. S. et al., *BioTechniques* 6:460–468 (1988), using modified T7 DNA polymerase (Sequence; US Biochemicals) and synthetic oligonucleotide primers. DNA sequence was assembled and analyzed using the Sequence Analysis Software Package of the Genetics Computer Group (version 6.2) on a VAX computer. Wordsearch and FastA routines using the algorithm of Wilbur and Lipman, Wilbur, W. J. et al., *PNAS (USA)* 80:726–730 (1983) and Pearson and Lipman, Pearson, W. R. et al., *PNAS (USA)* 85:2444–2448 (1988), respectively, were used in searches of homology to DNA and protein sequences contained within the following databases; GenBank (release 63.0), NBRF/PIR (release 23), DNA Database of Japan (May 15, 1990). In addition, the GenBank on-line service was used to search the Swiss Protein Database and translated GenBank (new sequences) on May 17, 1990 using the procedure of Pearson and Lipman, Pearson, W. R. et al., *PNAS (USA)* 85:2444–2448 (1988). Search for internal repeat and analysis of hydropathy were performed using standard methods discussed by Boguski, M. S. et al., *J. Lipid Res.* 27:1011–1034 (1986).

Southern Blot Analysis

Genomic Southern blot analysis was carried out in a standard fashion as described in Sambrook, J. et al., *Molecular Cloning: A laboratory manual.* Second Edition. Cold Spring Harbor Laboaratory, Cold Spring Harbor, N.Y. Human genomic DNA was isolated from 11B squamous carcinoma cells as described in Sambrook, J. et al., *Molecular Cloning: A laboratory manual.* Second Edition. Cold Spring Harbor Laboaratory, Cold Spring Harbor, N.Y. Genomic DNA from rabbit, macaque, rat, mouse, and Drosphila were gifts from Dr. Paul Killen and Dr. Patrick Venta.

Fusion-Protein Construction and Expression

Fusion protein vectors containing the Pst 1-Hind III fragment of B61 fused inframe to bacterial trpE were expressed in *E. coli*, with the use of a paTH-22 vector described in Diekmann, C. L. et al., *J. Biol. Chem.* 266:1513–1520 (1985) and Spindler, K. R. et al., *Vinol.* 49:132–141 (1984) See FIG. 6A and Results. Prior to expression, prospective clones were analyzed by restriction digest to assure that the cloning site was appropriately recreated and reading frame preserved. Transformed cells were grown in 10 ml of M9 media containing 1% Casamino Acids, 20 µg/ml tryptophan, and 150 µg/ml ampicillin. For induction, cells were pelleted, tryptophan was removed by washing the pellet in tryptophan-free media, and the culture was resuspended in 100 ml tryptophan-free media. Following an additional 1 h incubation, β-indole acrylic acid was added to 20 µg/ml and the incubation was continued for an additional 4 h. The relatively insoluble fusion protein product was partially purified from bacterial protein by lysing the cell pellet in lysozyme (3 mg/ml), sonicating (3 times for 15 s on ice), and successively washing with 20 ml ice cold 0.5% NP-40 in 0.3M NaCl in 10 mM Tris-HCl (pH 7.5), and with 10 mM Tris (pH 7.5). Samples were analyzed by SDS-polyacrylamide gel electrophoresis (PAGE) and Coomassie Blue R-100 staining.

Preparation of Polyclonal Immune Serum

TrpE-B61 fusion protein was isolated by SDS-PAGE and the protein bands lightly stained in water based Coomassie Blue. The appropriate band (approximately 400 µg) was cut out, homogenized, and mixed 1:1 with either complete or incomplete Freund's Adjuvant. This preparation was injected intramuscularly into the proximal lower extremities of New Zealand White female rabbits. A total of 6 boost immunizations were given at 4 week intervals. Rabbits were bled 2 weeks after immunizations.

Immune serum was analyzed by immunoblotting as described by Harlow, E., et al., *Antibodies: A Laboratory Manual*. Cold Spring Harbor Laboaratory, Cold Spring Harbor, N.Y.:471–510 (1988). Briefly, appropriate antigen was separated by SDS-PAGE, transferred to nitrocellulose using an LKB Multiphor II semidry electrophoresis apparatus (Pharmacia) according to the manufacturer's instruction, and blocked overnight in tris-buffered saline (pH 7.5) containing 3% nonfat dry milk. Following incubation in immune serum, blots were probed with horseradish peroxidase conjugated goat anti-rabbit IgG (BioRad) diluted 1:1000. Blots were developed with color development reagent containing 4-chloro-1-napthol (BioRad) and dilute hydrogen peroxide according to the manufacturer's directions.

Metabolic Radiolabelling and Immunoprecipitation

HUVE were metabolically labelled as described by Prochownik, E. V. et al., *J. Cell Biol.* 109:843–852 (1989), except labeling was performed in methionine-free, cysteine-free minimal essential media (Gibco, Select-Amine) supplemented with 50 µg/ml bovine serum albumin and 100 pCi/ml each of [$^{35}$S]methionine and [$^{35}$S]cysteine (Amersham). Conditioned media was collected, centrifuged to remove cell debris, and protease inhibitors added to final concentration of 1 mM phenylmethyl sulfonyl fluoride, 1 mM leupeptin, and 20 µg/ml pepstatin A. The cell layer was solubilized in 0.5% SDS and protease inhibitor cocktail added. Lysate DNA was sheared through a 23 gauge needle. The solubilized cell layer was made 0.1% SDS, 1% Triton X-100 and 0.5 % sodium deoxycholate and immunoprecipitated as 30 described by Prochownik, E. V. et al., *J. Cell Biol.* 109:843–852 (1989).

For the iodination of HUVE cells, plates were washed once in cold PBS, and cells removed from plates by incubation in PBS containing 1 mM EDTA at 4° C. for 15 min. Cells were pelleted at 1000 g for 5 min and washed three times in 5 ml cold PBS. Iodination with 130 µCi$^{125}$ sodium iodide (ICN, specific activity ≈17 Ci/mg I) was carried out in an iodogen tube using the method of Fraker and Speck, Fraker, P. J. et al., *Biochem. Biophys. Res. Commun.* 80:849–857 (1978) for 1 h on ice. Cells were washed 3 times in 12 ml ice cold 10 mM sodium thiosulfate in PBS and were finally solubilized in 0.5% SDS and protease inhibitor cocktail added.

RESULTS

Molecular Cloning and Sequencing of B61

Figure 2:
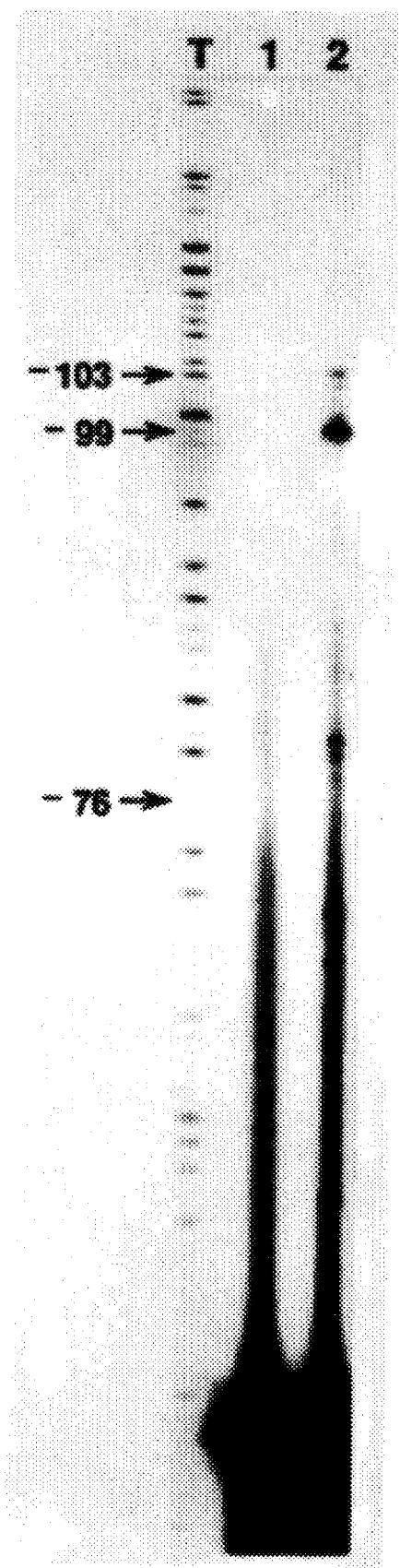
FIG. 2 is a primer extension analysis.
Figure 3B:
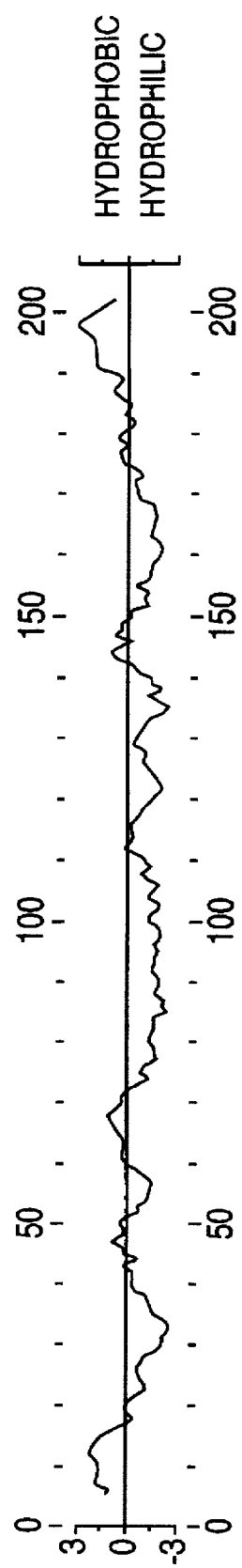
FIG. 3B is a plot of hydrophobicity of B61.

DNA probes obtained from the original B61 cDNA, B61.0 were used to rescreen a λgt11 library constructed with poly (A)$^+$ mRNA from human umbilical vein endothelial cells (HUVE) treated with both TNF-α and cycloheximide. Several additional clones were isolated, at least one of which, B61.1, contained the entire open reading frame for B61 (FIG. 1 ). In order to clone the 5' end of the cDNA, the polymerase chain reaction was employed using primers containing sequences from the 5' end of the partial B61 cDNA and sequences flanking the cloning site in the λgt11 vector. The λgt11 cDNA library was used as template DNA. Again several clones were obtained which allowed confirmation of the 5' most cDNA sequence. An analytical primer extension was carried out to assess the 5' extent of the B61 mRNA. (FIG. 2). Synthetic oligonucleotides (see FIG. 3, broken arrows) were 5' end labelled and hybridized to 30 µg total RNA obtained from HUVE cells pretreated for 2 hours with TNF (21 µg/ml) and CHX (10 µg/ml). Following reverse transcription, products were resolved on a 6% denaturing acrylamide gel.

FIG. 2 shows nucleotide base markers (lane T), a control experiment using 30 µg tRNA as template (lane 1) and primer extension using Primer I as described above (lane 2). The primer extension was repeated using a second primer (designated Primer II; see FIG. 3) and confirmed the results obtained with the first primer (not shown). Numbers represent distance in bases from the initiation codon.

In FIG. 1, a composite B61 mRNA is represented colinear with the four cDNA clones used to derive the B61 sequence. The composite B61 mRNA is depicted on top by the thin line with the predicted coding region expanded. As shown, the B61 mRNA extends an additional 25–29 bases 5' to the cloned B61 cDNA. Numbers represent nucleotide bases with adenosine in initiation ATG designated+1. Open boxes represent hydrophobic domains and stippled central box a hydrophilic domain; SP designates signal peptide. Potential site of N-liked glycosylation is marked above with dagger. The start of the polyA tail is marked AAAAA and the arrow preceding this indicated the site of the consensus polyadenylation signal (AAUAAA).

The portions of cDNA clones used for genomic Southern blot analyses and as an insert for fusion protein construction are shown above the restriction map of B61 cDNA clones. Bold lines indicate regions of each cDNA clone that were sequenced in both directions. The composite B61 mRNA sequence was derived by sequencing at least two coordinate cDNA's. The only difference in nucleotide sequence lie within the 3' untranslated region, where nucleotides in B61.0 differed from those in corresponding position in B61.1 (positions: 915, A to T; 1142, A to G). These may represent polymorphisms or errors made by reverse transcriptase during cDNA synthesis.

Structural Features

The B61 cDNA sequence and translation of the predicted open reading frame is presented in FIG. 3A. Amino acid numbering (right margin) begins at the initiator methionine, nucleotide numbering (left margin) begins at the initiation codon. Indicated with the amino acid sequence is the putative signal peptide (underlined) and a single N-linked glycosylation consensus (shaded box). Of note, the initiation codon is in agreement with Kozak's consensus sequence (solid overlined). The polyadenylation consensus sequence is underlined. Broken overlying arrows (I and II) denote regions used as primers in the primer extension experiment. Comparison of these sequences to both protein and DNA sequence data bases failed to identify related gene products of significant homology. It will be appreciated that the nucleotide and amino acid sequences of the present invention can include some variation, but must be "substantially similar" to those set forth in FIG. 3A and SEQ ID NOS:1 and 2. By "substantially similar" is meant that any variation therein does not significantly impair the sequence's functionality.

The B61 mRNA (including the uncloned extreme 5' untranslated region as defined by primer extension) extends over 524 nucleotide bases. It includes a 99 base GC rich (70% GC content) 5' untranslated region, a continuous open reading frame of 615 bases and a 3' untranslated region of 810 bases. Within the 3' untranslated region, a polyadenylation signal is found upstream of the poly A tail. No destabilization consensus sequence (UUAUUUAU) is present as identified by Caput, D. B. et al., *PNAS (USA)* 83:1670–1674 (1986).

The assigned initiation codon represents the 5' most AUG encountered and is located within a sequence context favorable to translation initiation as defined by Kozak, M., *J. Cell Biol.* 108:229–241 (1989). Confirmation of the reading frame determined by the putative initiation AUG is provided by the observation (see below) that a polyclonal immune serum, generated to a fusion protein constructed in the same reading frame, immunoprecipitates specifically a protein of the appropriate molecular weight from human endothelium.

The predicted open reading frame encodes a polypeptide of 205 amino acids with an estimated molecular weight of 24 kDa. An analysis of hydrophobicity of the B61 amino acid sequence shown in FIG. 3A demonstrates that B61 contains markedly hydrophobic N-terminal and C-terminal regions. The plot in FIG. 3B was generated with the algorithm of Kyte and Doolittle, Kyte, J. et al., *J. Mol. Biol.* 157:105–132 (1982). Numbering on abscissa represents amino acid residue and positive values represent hydrophobic regions. (Window of averaging=9). The 18 amino acid N-terminal hydrophobic region closely fits von Heinje's consensus for a signal peptide, von Heijne, G., *J. Mol. Biol.* 184:99–105 (1985). Comparison with known signal peptides reveals that cleavage likely follows the (−3,−1) rule as discussed by von Heijne, G., *Nucl. Acids Res.* 14:4683–4690 (1986) and precedes the aspartic acid residue in position 19. Cleavage of the signal peptide would therefore form a mature protein of 187 amino acids and predicted molecular weight of 22 kDa.

The C-terminal hydrophobic region spans 23 amino acid residues but does not appear to be a transmembrane domain. Unlike known transmembrane segments, this hydrophobic region is interrupted by several polar amino acids, extends to the extreme C-terminus and is not followed by a cluster of basic amino acid residues. There is structural similarity to the C-terminal region of glycosyl-phospatidylinositol (GPI) linked membrane anchored proteins as discussed by Ferguson, M. A. et al., *Ann. Rev. Biochem.* 57:285–320 (1988).

The remainder of the molecule is predominantly hydrophilic. A single consensus sequence for N-linked glycosylation exists near the N-terminus of the mature protein. There appears to be no significant internal repeat motifs as judged by self comparison using Maizel and Link's dot matrix analysis from Maizel, J. V. et al., *PNAS (USA)* 78:7665–7669 (1981).

Uniqueness and Conservation of B61 Gene

Figure 4:
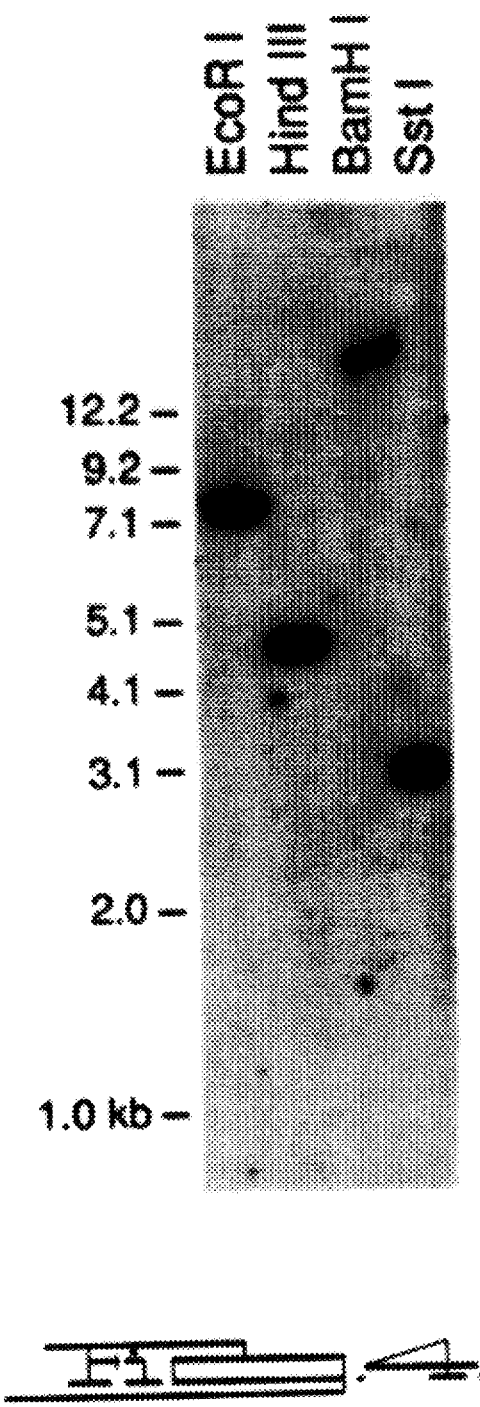
FIG. 4 is a genomic Southern analysis demonstrating that B61 is a single copy gene.

Genomic Southern blots of DNA from 11B human squamous carcinoma cell were hybridized with cDNA probes "A" or B61.1 (as defined in FIG. 1). Genomic DNA isolated from 11B human squamous carcinoma cells was digested with either EcoRI, Hind III, BamHI, or Sst 1 restriction endonuclease. Ten μg of each sample was resolved on a 0.6% agarose gel, transferred to nitrocellulose and hybridized to a $^{32}$P-labelled 300 bp fragment (see FIG. 1, Fragment A) under high stringency conditions (hybridization buffer including 5× SSC and 50% formamide at 42° C.; wash buffer including 0.1× SSC and 0.1% SDS at 65° C.). The film exposure was 16 h at −80° C. with intensifying screen. As shown in FIG. 4, the A probe, comprising a 300 nucleotide segment representing the 3' half of the open reading frame, recognized discrete genomic fragments in each of four genomic DNA restriction digests. Labelled B61.1 cDNA was used to probe an identical Southern blot (not shown). Several additional hybridizing fragments were identified. Screening at reduced stringency (2× SSC, room temperature), did not result in the appearance of additional bands. Thus, B61 is a single-copy gene which does not appear to be a member of a family of evolutionarily related proteins.

Figure 5:
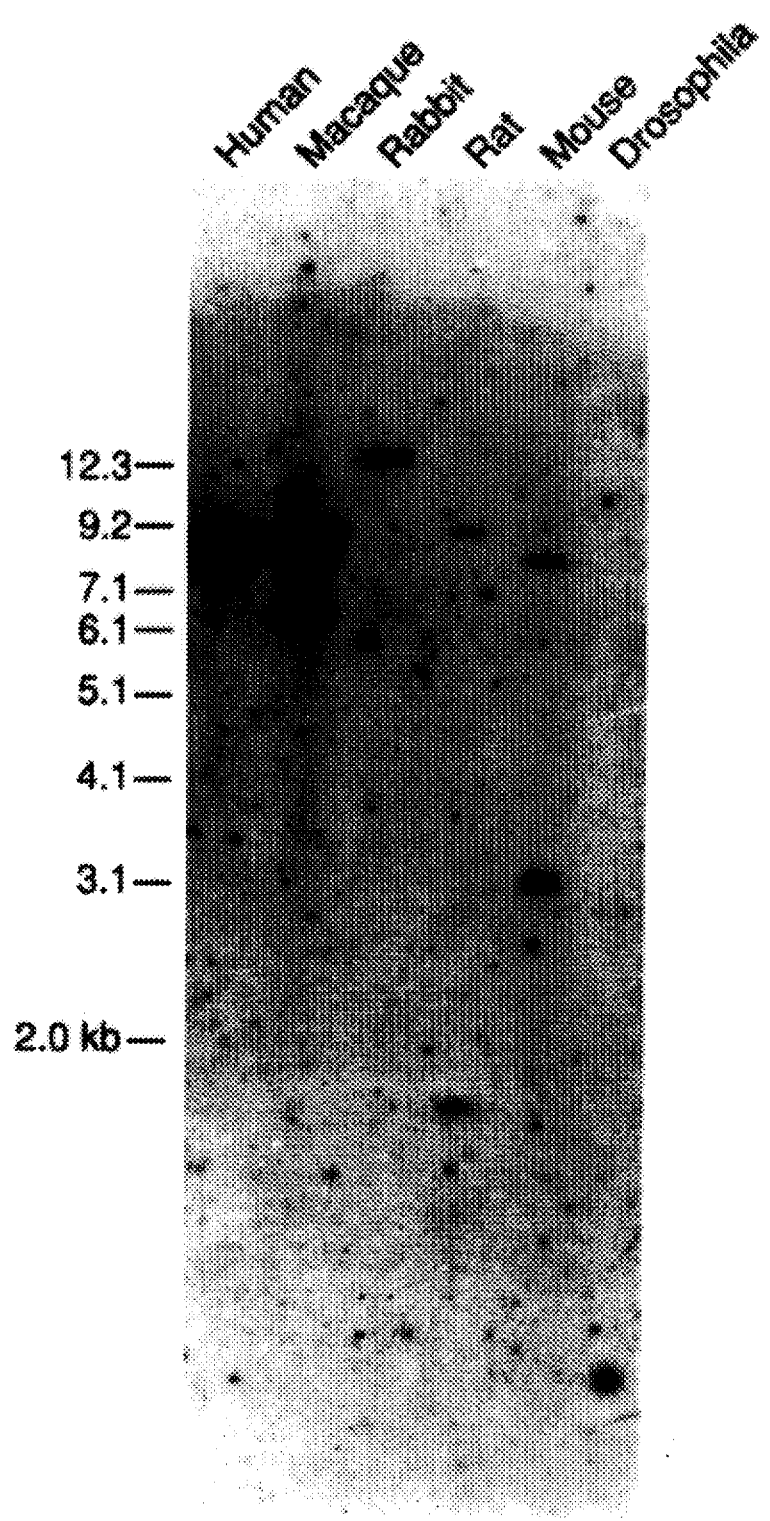
FIG. 5 is a genomic Southern analysis demonstrating the evolutionary conservation of B61.

FIG. 5 shows a Southern blot of EcoRI digested genomic DNA obtained from several animal species. Ten/μg of genomic DNA isolated from cells representing the various animal species shown was digested with EcoRI, resolved on a 0.6% agarose gel, transferred to nitrocellulose and hybridized to a $^{32}$P labelled B61.0 cDNA. After hybridization, at 42° C. in 5× SSC and 50% formamide, a successive series of washes from low to high stringency (2× SCC at room temperature to 0.1× SSC at 65° C.) were carried out. Shown is the autoradiograph of the blot after washing at 1× SSC at 55° C. Film exposure was 3 days at −80° C. with intensifying screens. No additional bands were detected on lower stringency washes in any species including Drosphilia. DNA fragments were identified in all species except Drosophila. Thus, the sequence and gene structure of B61 appear to have been conserved during evolution.

Generation of Polyclonal Immune Serum to B61

To provide a reagent for further characterization of the B61 protein, rabbit antisera to a bacterial fusion protein were prepared. A Pst I-Hind III restriction fragment was ligated into a bacterial MpE expression vector, fusing the bacterial trpE protein with the open reading frame encoding amino acid residues 15 to 205 of B61. This construct encoded the entire polypeptide sequence of the predicted mature form of B61. The pATH-B61 fusion protein was expressed in *E. Coli*.

Figure 6A:
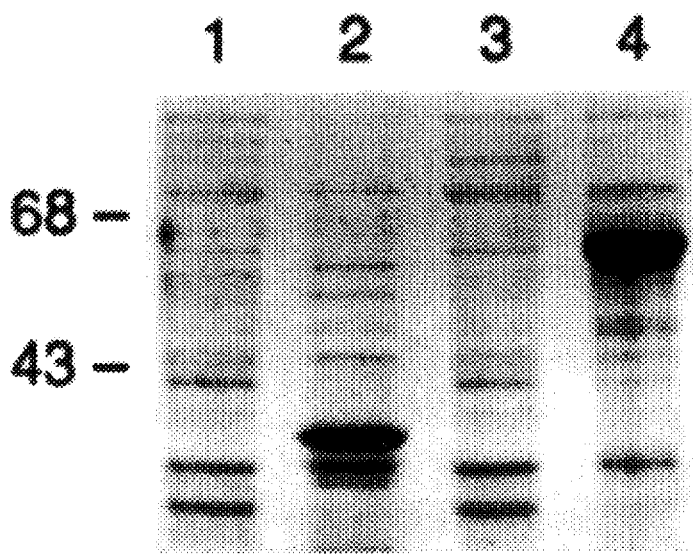
FIG. 6A illustrates the expression of pATH-B61 fusion protein in *E. Coli*.

FIG. 6 shows Coomassie Blue stained 10% SDS-polyacrylamide gel electrophoresis showing expression of pATH-B61 fusion protein. A B61 Pst I-Hind III insert (see FIG. 1) was subcloned into a pATH-22 bacterial fusion protein expression vector and transformed into DH5-α cells. After growth to $OD_{600}$=0.5 the appropriate cultures were induced by the removal of tryptophan and the addition of β-indole acrylic acid. Following an additional 4 h incubation insoluble protein was prepared and analyzed as previously described in "Materials and Methods". Shown in FIG. 6A: lane 1, pATH-22 vector alone, uninduced; lane 2, pATH-22 vector alone, induced; lane 3, pATH-B61 fusion protein construct, uninduced; lane 4, pATH-B61 fusion protein construct, induced. Relative molecular mass standards are shown to the left.

After expression in *E. Coli* (FIG. 6A), the insoluble trpE-B61 fusion protein was dissolved in SDS sample buffer, fractionated by SDS-polyacrylamide electrophoresis, and the band cut from preparative gels used to immunize rabbits.

Figure 6B:
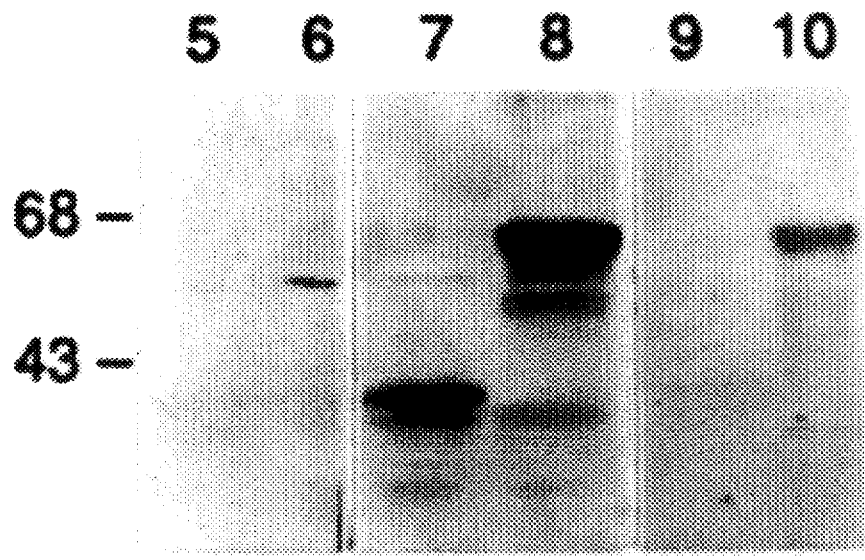
FIG. 6B presents immunoblots illustrating the specificity of rabbit polyclonal serum to B61.

The presence of monospecific antibodies to B61 was determined by immunoblotting as shown in FIG. 6B. Immune serum was prepared from rabbits injected with gel purified preparations of the pATH-B61 fusion protein, as described above. Protein derived from bacterial preparations containing induced pATH-22 alone (lanes 5, 7, 9; equivalent to lane 2) and protein derived from preparations containing induced pATH-B61 (lanes 6, 8, 10; equivalent to lane 4) were reduced and resolved on SDS-PAGE and transferred to nitrocellulose. These were blotted with preimmune rabbit serum (lanes 5 and 6), B61 immune serum (lanes 7 and 8), or with B61 immune serum preincubated with protein derived from a bacterial preparation containing induced pATH-22 (equivalent to 8-fold excess of lane 2)(lane 9 and 10). The polyclonal immune serum recognized a band corresponding to the trpE bacterial backbone as well as a band corresponding to the trpE-B61 fusion protein (FIG. 6B, lane 10), confirming the presence of antibodies to the B61 portion of the fusion protein. Further evidence that the polyclonal serum contained monospecific antibodies to B61 was demonstrated by immunoblotting to a second fusion protein, constructed in an alternate bacterial expression system that contained the B61 sequence fused to an alternate bacterial protein backbone (data not shown).

Immunoprecipitation Demonstrating that B61 is a Secreted Protein

In order to localize the B61 protein, HUVE cells were metabolically labelled and immunoprecipitated as described below. HUVE cells were deprived of endothelial cell growth factor overnight, then stimulated (lanes 6–10) with TNF-α (20 ng/ml) for 2 hours. Cells were metabolically labelled with [$^{35}$S]methionine, 100 μCi/ml in the presence or absence of TNF-α for 6 h, then chased for 6 h. Conditioned media ($7 \times 10^6$ cpm) and cell layers ($5 \times 10^7$ cpm) were immunoprecipitated as indicated below, the precipitated material was reduced and resolved by 12.5% SDS-PAGE, and visualized by autoradiography: lanes 1, 3, 6, 9: immunoprecipitated with preimmune rabbit serum; lanes 2, 4, 7, 10: B61 immune serum; lanes 3, 8: B61 immune serum preincubated with pATH-B61 fusion protein (equivalent to FIG. 6A, lane 4). Relative molecular mass standards are indicated at the left.

Figure 7:
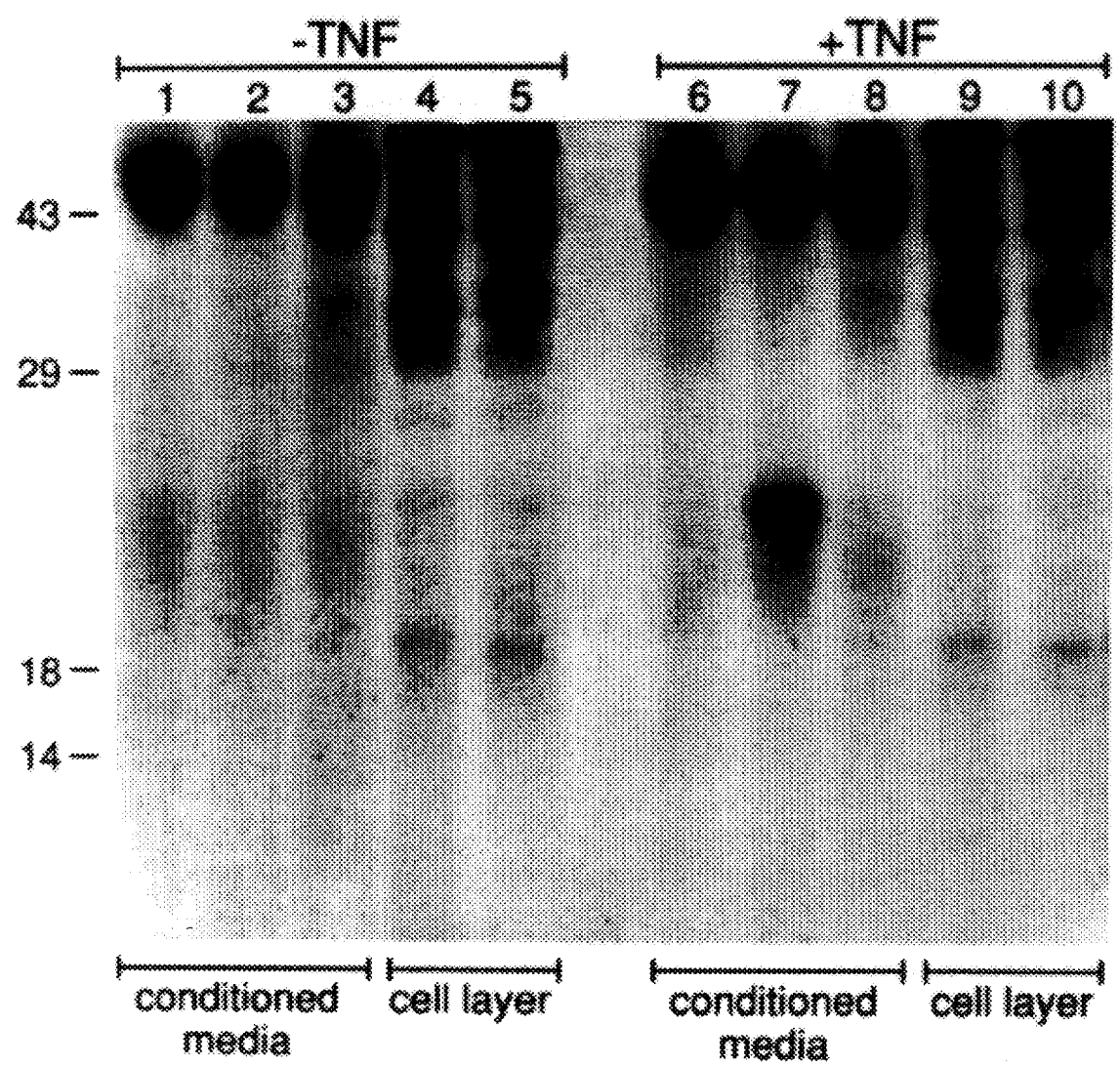
FIG. 7 shows the result of a pulse-chase experiment demonstrating that B61 is a secreted protein without detectable membrane association.

After TNF stimulation, 6 h metabolic labelling and 6 h chase, a protein was precipitated only from the conditional media (compare lanes 7 and 9 of FIG. 7). This protein migrated at an apparent molecular weight of B61 predicted from primary structure. Precipitation of this band was specifically blocked by preincubating B61 antisera with a molar excess of the trpE-B61 fusion protein (FIG. 7, lane 8).

In the pulse-chase experiment presented in FIG. 7, B61 does not appear to be significantly associated with the cell layer. Indeed, a three week exposure of this gel failed to allow detection of cell associated B61. However, given the similarity of B61's C-terminal hydrophobic region to the C-terminal regions found in GPI linked membrane anchored proteins described by Ferguson, M. A. et al., *Ann. Rev. Biochem.* 57:285–320 (1988), an alternate experimental approach was used to confirm that B61 is not plasma membrane associated. Intact TNF-stimulated HUVE cells were surfaced iodinated, detergent solubilized, and the solubilized fraction immunoprecipitated with B61 antisera. Immunoprecipitated proteins were reduced and resolved by SDS-PAGE and visualized by autoradiography. Labelled B61 was not detected in the immunoprecipitated material. From the accumulated evidence, it appears that B61 is a secreted protein without detectable membrane association.

Finally, B61 expression and secretion is markedly induced after TNF stimulation in HUVE (compare lanes 2 and 7, FIG. 7). This is in concordance with previously published Northern blot analysis data which demonstrates significant induction of B61 mRNA following TNF stimulation. See Dixit, V. M. et al., *J. Biol. Chem.* 264:16905–16909 (1989).

Detection of B61 Transcript in Tissue

The B61 transcript in biopsy materials, such as, e.g., that from temporal arteritis or kidney rejection, can be detected by in situ hybridization. This technique allows for the detection and quantitation of mRNA transcript in tissues. Detection is achieved by autoradiographically monitoring the binding of a labelled antisense B61 probe, preferably of eight or more nucleic acids, to endogenous B61 transcript. The antisense B61 probe is generated by cloning the cDNA for B61 into a vector containing flanking SP6 and T7 promotors. In the presence of the appropriate polymerase (e.g., SP6 or T7) and radionucleotides, a labelled antisense probe is generated. The probe is then used under conditions of high stringency, e.g., 50% formamide; 42° C., such that it will specifically bind to B61 transcript. Since the probe is radiolabelled, a quantitative signal is detectable and there will be a direct correlation between the degree of inflammation and the amount of B61 transcript detected.

Quantitation of B61 Protein in Body Fluids

B61 protein in body fluids such as plasma, urine or cerebrospinal fluid can be quantitated using a radioimmunoassay. This assay employs polyclonal anti-B61 antibody with a standard curve generated by using the bacterially expressed form of B61. It will, however, be appreciated that monoclonal antibodies can also be employed in an assay of the present invention. In the assay herein described, the binding of radioiodinated B61 to antibody is competed for with known amounts of unlabelled B61 protein. Data from such an experiment allows the generation of a standard curve. Given the degree of competition by a sample, it is possible to extrapolate from the standard curve the amount of B61 actually present in the sample. The amount of B61 in body fluid samples will correlate with the degree or severity of the inflammatory disease process.

It will be appreciated that the foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

---

What is claimed is:

1. A method of assaying for the presence of B61 in a patient comprising the steps of:
    a) providing an antibody to B61;
    b) obtaining a sample of the patient's blood or tissue;
    c) contacting the sample under conditions favorable for binding of the antibody to any B61 in the sample; and
    d) detecting the binding of the antibody, the presence of bound antibody being a positive indication of the presence of B61 in the sample.

2. The method of claim 1 further comprising the step of:
    e) quantifying binding of the antibody to B61.

3. An isolated polypeptide comprising an amino acid sequence encoded by the nucleotide sequence shown in SEQ ID NO: 1 from nucleotide 74 to nucleotide 1497.

4. An isolated polypeptide comprising an amino acid sequence encoded by the nucleotide sequence shown in SEQ ID NO: 1 from nucleotide 127 to nucleotide 1497.

5. An isolated polypeptide comprising the amino acid sequence shown in SEQ. ID NO:2.

6. An isolated polypeptide comprising an amino acid encoded by a nucleotide sequence complementary under conditions of high stringency to the nucleotide sequence shown in SEQ ID NO: 1 from nucleotide 74 to nucleotide 1497.

7. An isolated polypeptide comprising an amino acid encoded by a nucleotide sequence complementary under conditions of high stringency to the nucleotide sequence shown in SEQ ID NO: 1 from nucleotide 127 to nucleotide 1497.

8. An isolated polypeptide comprising an amino acid encoded by at least 30 nulceotides of the sequence shown in SEQ ID NO: 1 from nucleotide 74 to nucleotide 1497.

9. An antibody raised to the isolated polypeptide of claim 8.

10. An isolated polypeptide comprising an amino acid encoded by at least 30 nucleotides of a nucleic acid complementary under conditions of high stringency to the sequence shown in SEQ ID NO: 1 from nucleotide 74 to nucleotide 1497.

11. An antibody raised to the isolated polypeptide of claim 10.

12. The antibody of claim 11, wherein the antibody is a polyclonal antibody or a monoclonal antibody.

13. Purified B61 protein.

14. An isolated polypeptide, produced by the method comprising:
   introducing a nucleic acid of at least 30 nucleotides of the nucleotide sequence shown in SEQ ID NO: 1 from nucleotide 74 to nucleotide 1497 into a bacterial cell under conditions favorable for transcription and translation of the nucleic acid; and
   b) isolating the polypeptide so produced.

* * * * *

UNITED STATES PATENT AND TRADEMARK OFFICE
CERTIFICATE OF CORRECTION

PATENT NO. : 5,688,656
DATED : November 18, 1997
INVENTOR(S) : Vishva M. Dixit

It is certified that error appears in the above-identified patent and that said Letters Patent is hereby corrected as shown below:

Column 4, line 1, "a-plasma" should be --a plasma--
      line 53, "Endothelial Cells" should be on a separate line as a new title
      line 54, "studies:" should be --studies.--

Signed and Sealed this

Third Day of March, 1998

Attest:

Attesting Officer

BRUCE LEHMAN
Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1498 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 74..688

( i x ) FEATURE:
        ( A ) NAME/KEY: mat_peptide
        ( B ) LOCATION: 128

( x i ) SEQUENCE DESCRIPTION: SEQ ID NO:1:

```
GCGGAGAAAG CCAGTGGGAA CCCAGACCCA TAGGAGACCC GCGTCCCCGC TCGGCCTGGC        60

CAGGCCCCGC GCT ATG GAG TTC CTC TGG GCC CCT CTC TTG GGT CTG TGC        109
            Met Glu Phe Leu Trp Ala Pro Leu Leu Gly Leu Cys
            -18     -15                 -10

TGC AGT CTG GCC GCT GCT GAT CGC CAC ACC GTC TTC TGG AAC AGT TCA        157
Cys Ser Leu Ala Ala Ala Asp Arg His Thr Val Phe Trp Asn Ser Ser
    -5              1               5                       10

AAT CCC AAG TTC CGG AAT GAG GAC TAC ACC ATA CAT GTG CAG CTG AAT        205
Asn Pro Lys Phe Arg Asn Glu Asp Tyr Thr Ile His Val Gln Leu Asn
            15              20                      25

GAC TAC GTG GAC ATC ATC TGT CCG CAC TAT GAA GAT CAC TCT GTG GCA        253
Asp Tyr Val Asp Ile Ile Cys Pro His Tyr Glu Asp His Ser Val Ala
            30              35                      40

GAC GCT GCC ATG GAG CAG TAC ATA CTG TAC CTG GTG GAG CAT GAG GAG        301
Asp Ala Ala Met Glu Gln Tyr Ile Leu Tyr Leu Val Glu His Glu Glu
            45              50                      55

TAC CAG CTG TGC CAG CCC CAG TCC AAG GAC CAA GTC CGC TGG CAG TGC        349
Tyr Gln Leu Cys Gln Pro Gln Ser Lys Asp Gln Val Arg Trp Gln Cys
    60              65                      70

AAC CGG CCC AGT GCC AAG CAT GGC CCG GAG AAG CTG TCT GAG AAG TTC        397
Asn Arg Pro Ser Ala Lys His Gly Pro Glu Lys Leu Ser Glu Lys Phe
75              80                      85                      90

CAG CGC TTC ACA CCT TTC ACC CTG GGC AAG GAG TTC AAA GAA GGA CAC        445
Gln Arg Phe Thr Pro Phe Thr Leu Gly Lys Glu Phe Lys Glu Gly His
                95              100             105

AGC TAC TAC TAC ATC TCC AAA CCC ATC CAC CAG CAT GAA GAC CGC TGC        493
Ser Tyr Tyr Tyr Ile Ser Lys Pro Ile His Gln His Glu Asp Arg Cys
                110             115                     120

TTG AGG TTG AAG GTG ACT GTC AGT GGC AAA ATC ACT CAC AGT CCT CAG        541
Leu Arg Leu Lys Val Thr Val Ser Gly Lys Ile Thr His Ser Pro Gln
        125             130                     135

GCC CAT GTC AAT CCA CAG GAG AAG AGA CTT GCA GCA GAT GAC CCA GAG        589
Ala His Val Asn Pro Gln Glu Lys Arg Leu Ala Ala Asp Asp Pro Glu
        140             145                     150

GTG CGG GTT CTA CAT AGC ATC GGT CAC AGT GCT GCC CCA CGC CTC TTC        637
Val Arg Val Leu His Ser Ile Gly His Ser Ala Ala Pro Arg Leu Phe
155             160                     165                     170

CCA CTT GCC TGG ACT GTG CTG CTC CTT CCA CTT CTG CTG CTG CAA ACC        685
Pro Leu Ala Trp Thr Val Leu Leu Leu Pro Leu Leu Leu Leu Gln Thr
                175             180                     185

CCG TGAAGGTGTA TGCCACACCT GGCCTTAAAG AGGGACAGGC TGAAGAGAGG            738
Pro

GACAGGCACT CCAAACCTGT CTTGGGGCCA CTTTCAGAGC CCCCAGCCCT GGGAACCACT     798

CCCACCACAG GCATAAGCTA TCACCTAGCA GCCTCAAAAC GGGTCAGTAT TAAGGTTTTC     858

AACCGGAAGG AGGCCAACCA GCCCGACAGT GCCATCCCCA CCTTCACCTC GGAGGGACGG     918

AGAAAGAAGT GGAGACAGTC CTTTCCCACC ATTCCTGCCT TTAAGCCAAA GAAACAAGCT     978

GTGCAGGCAT GGTCCCTTAA GGCACAGTGG GAGCTGAGCT GGAAGGGGCC ACGTGGATGG    1038

GCAAAGCTTG TCAAAGATGC CCCCTCCAGG AGAGAGCCAG GATGCCCAGA TGAACTGACT    1098

GAAGGAAAAG CAAGAAACAG TTTCTTGCTT GGAAGCCAGG TACAGGAGAG GCAGCATGCT    1158

TGGGCTGACC CAGCATCTCC CAGCAAGACC TCATCTGTGG AGCTGCCACA GAGAAGTTTG    1218

TAGCCAGGTA CTGCATTCTC TCCCATCCTG GGCAGCACT CCCAGAGCT GTGCCAGCAG      1278

GGGGCTGTG CCAACCTGTT CTTAGAGTGT AGCTGTAAGG GCAGTGCCCA TGTGTACATT     1338
```

-continued

| | | | | | |
|---|---|---|---|---|---|
| CTGCCTAGAG | TGTAGCCTAA | AGGGCAGGGC | CCACGTGTAT | AGTATCTGTA | TATAAGTTGC | 1398
| TGTGTGTCTG | TCCTGATTTC | TACAACTGGA | GTTTTTTAT  | ACAATGTTCT | TTGTCTCAAA | 1458
| ATAAAGCAAT | GTGTTTTTC  | GGAAAAAAAA | AAAAAAAAA  |            |            | 1498

( 2 ) INFORMATION FOR SEQ ID NO:2:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Glu   Phe   Leu   Trp   Ala   Pro   Leu   Leu   Gly   Leu   Cys   Cys   Ser   Leu   Ala
-18         -15                           -10                           -5

Ala   Ala   Asp   Arg   His   Thr   Val   Phe   Trp   Asn   Ser   Ser   Asn   Pro   Lys   Phe
            1                       5                       10

Arg   Asn   Glu   Asp   Tyr   Thr   Ile   His   Val   Gln   Leu   Asn   Asp   Tyr   Val   Asp
15                            20                    25                                  30

Ile   Ile   Cys   Pro   His   Tyr   Glu   Asp   His   Ser   Val   Ala   Asp   Ala   Ala   Met
                        35                            40                            45

Glu   Gln   Tyr   Ile   Leu   Tyr   Leu   Val   Glu   His   Glu   Glu   Tyr   Gln   Leu   Cys
                  50                            55                      60

Gln   Pro   Gln   Ser   Lys   Asp   Gln   Val   Arg   Trp   Gln   Cys   Asn   Arg   Pro   Ser
            65                            70                            75

Ala   Lys   His   Gly   Pro   Glu   Lys   Leu   Ser   Glu   Lys   Phe   Gln   Arg   Phe   Thr
      80                            85                      90

Pro   Phe   Thr   Leu   Gly   Lys   Glu   Phe   Lys   Glu   Gly   His   Ser   Tyr   Tyr   Tyr
95                            100                   105                               110

Ile   Ser   Lys   Pro   Ile   His   Gln   His   Glu   Asp   Arg   Cys   Leu   Arg   Leu   Lys
                        115                         120                         125

Val   Thr   Val   Ser   Gly   Lys   Ile   Thr   His   Ser   Pro   Gln   Ala   His   Val   Asn
                  130                         135                         140

Pro   Gln   Glu   Lys   Arg   Leu   Ala   Ala   Asp   Asp   Pro   Glu   Val   Arg   Val   Leu
            145                         150                         155

His   Ser   Ile   Gly   His   Ser   Ala   Ala   Pro   Arg   Leu   Phe   Pro   Leu   Ala   Trp
      160                         165                         170

Thr   Val   Leu   Leu   Leu   Pro   Leu   Leu   Leu   Leu   Gln   Thr   Pro
175                           180                         185
```